(12) United States Patent
Rezachek

(10) Patent No.: US 8,661,874 B2
(45) Date of Patent: Mar. 4, 2014

(54) PHOTOACOUSTIC DETECTOR WITH BACKGROUND SIGNAL CORRECTION

(75) Inventor: Thomas M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 280 days.

(21) Appl. No.: 13/096,911

(22) Filed: Apr. 28, 2011

(65) Prior Publication Data

US 2012/0272717 A1 Nov. 1, 2012

(51) Int. Cl.
*G01N 21/17* (2006.01)

(52) U.S. Cl.
USPC ...................................... 73/24.02

(58) Field of Classification Search
USPC ............... 73/24.01, 24.02, 24.03; 250/343; 356/432
See application file for complete search history.

(56) References Cited

U.S. PATENT DOCUMENTS

| | | | |
|---|---|---|---|
| 6,006,585 A * | 12/1999 | Forster | 73/24.01 |
| 6,335,943 B1 * | 1/2002 | Lorraine et al. | 372/28 |
| 6,387,059 B1 * | 5/2002 | Marchitto et al. | 600/573 |
| 7,069,769 B2 * | 7/2006 | Kung | 73/24.02 |
| 7,089,781 B2 * | 8/2006 | Petrovic et al. | 73/31.05 |
| 7,213,444 B2 * | 5/2007 | Baraket et al. | 73/24.01 |
| 7,474,408 B2 * | 1/2009 | Alphonse | 356/479 |
| 7,525,661 B2 * | 4/2009 | Mandelis et al. | 356/432 |
| 7,782,462 B2 * | 8/2010 | Pavlovsky | 356/437 |
| 7,808,640 B2 * | 10/2010 | Fritz et al. | 356/432 |
| 2002/0171834 A1 * | 11/2002 | Rowe et al. | 356/418 |
| 2004/0127777 A1 * | 7/2004 | Ruchti et al. | 600/316 |
| 2004/0179200 A1 * | 9/2004 | Yoon et al. | 356/432 |
| 2004/0207409 A1 * | 10/2004 | Ariav et al. | 324/642 |
| 2005/0121614 A1 | 6/2005 | Stuttard | 250/343 |
| 2005/0160791 A1 * | 7/2005 | Kung | 73/24.02 |
| 2006/0254340 A1 * | 11/2006 | Baraket et al. | 73/24.01 |
| 2007/0049809 A1 * | 3/2007 | Bechtel et al. | 600/316 |
| 2007/0076208 A1 * | 4/2007 | Koo | 356/451 |
| 2008/0032412 A1 * | 2/2008 | Lewis et al. | 436/164 |
| 2009/0015819 A1 * | 1/2009 | Van Beek et al. | 356/39 |
| 2009/0320561 A1 | 12/2009 | Fritz et al. | 73/24.02 |
| 2010/0020326 A1 * | 1/2010 | Van Kesteren | 356/437 |
| 2010/0027012 A1 | 2/2010 | Fritz et al. | 356/432 |
| 2010/0045998 A1 | 2/2010 | Fritz et al. | 356/450 |
| 2010/0147051 A1 | 6/2010 | Tobias | 73/24.02 |
| 2010/0305741 A1 * | 12/2010 | Myrick | 700/110 |

* cited by examiner

*Primary Examiner* — John Fitzgerald
(74) *Attorney, Agent, or Firm* — Husch Blackwell LLP

(57) ABSTRACT

A photoacoustic detector includes a sensing region for receiving atmospheric samples. Radiant energy from a source is directed toward the sensing region. A thermal isolator and a displaced optical filter are positioned between the incoming radiant energy and the sensing region so that the radiant energy passes, at least in part, through both elements.

17 Claims, 3 Drawing Sheets

PHOTOACOUSTIC DETECTOR WITH BACKGROUND SIGNAL CORRECTION

FIELD

This application pertains to photoacoustic detectors. More particularly, the application pertains to such detectors which include circuitry to remove background noise.

BACKGROUND

Various types of photoacoustic sensors are known to detect gases. These include, Fritz et al., U.S. Patent Application No. 2009/0320561, published Dec. 31, 2009 and entitled "Photoacoustic Cell"; Fritz et al., U.S. Patent Application No. 2010/0027012, published Feb. 4, 2010 and entitled, "Photoacoustic Spectroscopy System"; Fritz et al., U.S. Patent Application No. 2010/0045998, published Feb. 25, 2010 and entitled "Photoacoustic Sensor". The above noted published applications have been assigned to the assignee hereof, and are incorporated herein by reference.

Such sensors, while useful, can be affected by thermally generated noise. Such noise can create errors in output signals indicative of ambient sensed gas.

DETAILED DESCRIPTION

Figure 1:
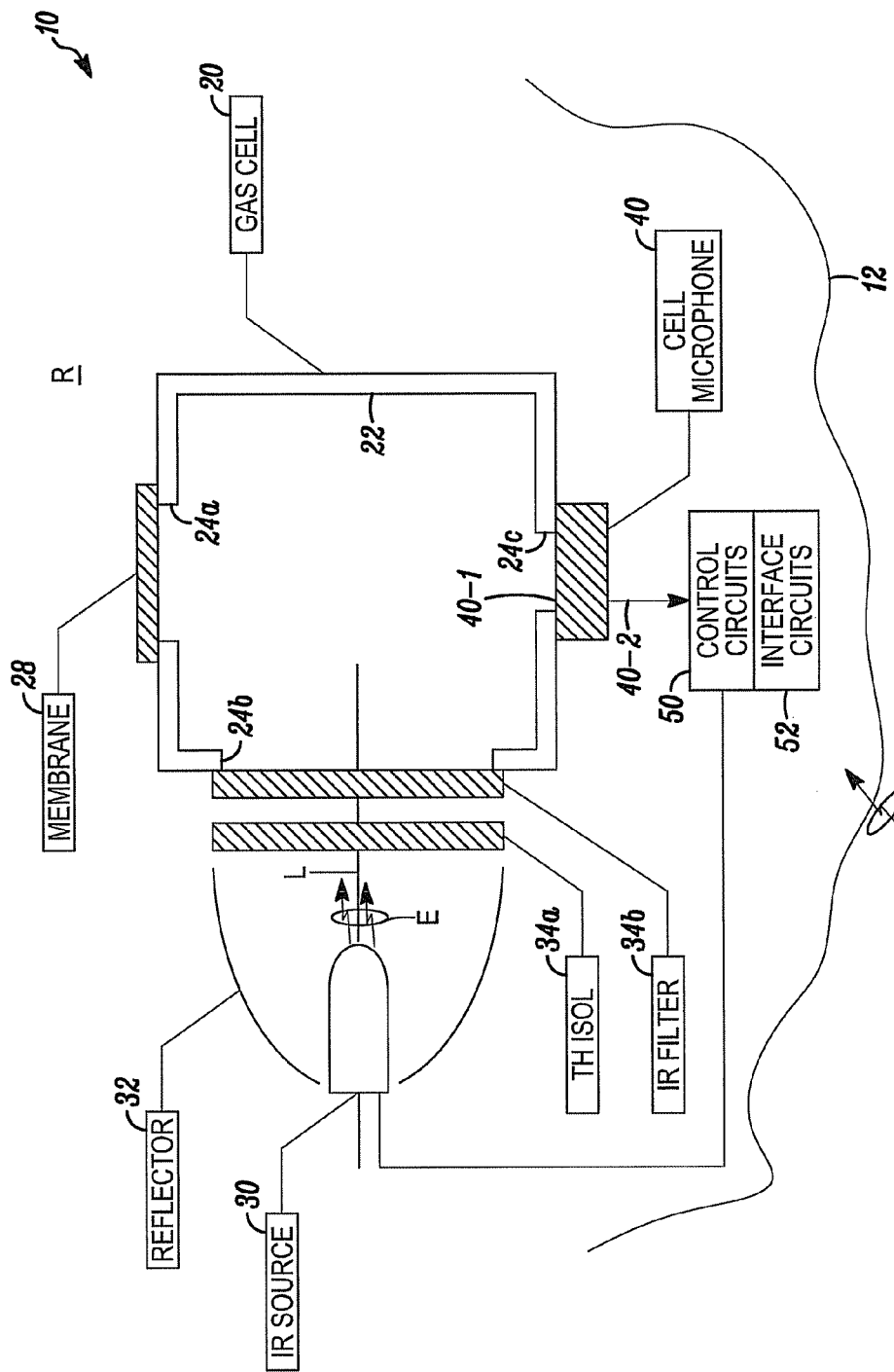
FIG. 1 is a block diagram of a detector in accordance herewith.

While embodiments can take many different forms, specific embodiments thereof are shown in the drawings and will be described herein in detail with the understanding that the present disclosure is to be considered as an exemplification of the principles hereof, as well as the best mode of practicing same. No limitation to the specific embodiment illustrated is intended.

In a disclosed embodiment, thermally induced noise can be substantially reduced or eliminated in a photoacoustic detector by using two spaced apart, radiant energy transmissive elements. One element can be an optical window with high transmissivity at a pre-determined wavelength. The second element, displaced from the window, can be implemented as an optical filter.

As radiant energy from a local source falls on the optical window it, in part, passes through the window. A larger portion of the incident energy results in heating the optical window. The radiant energy which has passed through the window is incident on the optical filter. It, in part passes though the filter into a gas sensing cell or chamber.

The presence of the displaced optical window thermally isolates the filter, which could be an infra-red filter for example, which is in contact with the test gas in the cell or chamber. This structure substantially eliminates any error signal produced by heating of the filter.

FIG. 1 illustrates an embodiment 10 of a photoacoustic detector in accordance herewith. Detector 10 can include a housing 12 suitable for portable or fixed use such as by attachment to a wall, ceiling or other mounting structure as desired. Detector 10 can monitor gas concentration in a region R.

Detector 10 includes a sensing chamber, or gas cell 20. The cell 20 can have a variety of shapes as would be understood by those of skill in the art. The shape of the cell 20 is exemplary only.

Cell 20 defines an internal region indicated generally at 22 with an atmospheric/environmental input port 24a. Port 24a is covered by a gas permeable membrane 28.

Cell 20 defines a light, or radiant energy input port 24b which can receive infra-red radiant energy from a source 30. Radiant energy E from the source 30 can be focused by a reflector 32. Radiant energy E incident on a thermal isolator 34a passes in part therethrough. The remaining incident energy E heats the isolator 34a thereby thermally isolating optical filter 34b therefrom.

A portion of the remaining radiant energy E is incident on the filter 34b, carried by the cell 20 and sealed to the port 24b. The portion of the radiant energy that is transmitted through the filter 34b enters the cell 20 and heats a subject gas therein as would be understood by those of skill in the art.

As illustrated in FIG. 1, source 30, isolator 34a, filter 34b and optical input port 24b lie on a common line L. While other configurations come within the spirit and scope hereof, locating the isolator 34a between the radiant energy source, such as infra-red source 30 with the isolator 34a displaced from filter 34b substantially eliminates heating of the filter 34b.

Cell 20 also defines an acoustic port 24c to which is coupled a microphone 40. The microphone 40 has an audio input port 40-1

Control circuitry 50 can be coupled to source 30 so as to modulate same at a selected frequency, as would be understood by those of skill in the art. An output signal 40-2 from the microphone 40 provides an indicium to control circuits 50 as to a level of gas concentration in the region 22.

Also as would be understood by those of skill in the art the control circuitry 50 can include wired or wireless interface circuitry 52 so that the detector 10 can communicate with an associated monitoring system, or diagnostic and test equipment via a wired or wireless medium 54.

Figure 2:
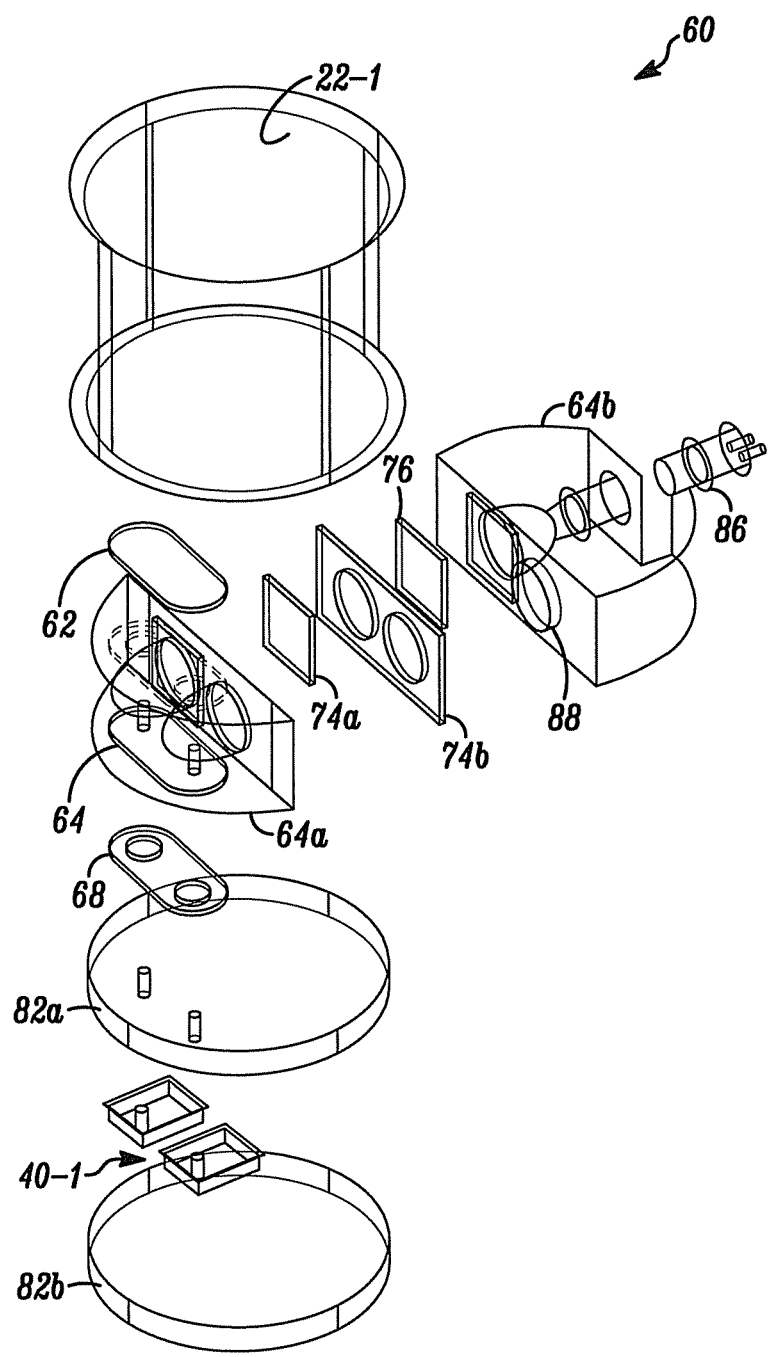
FIG. 2 is a diagram of another detector in accordance herewith.

FIG. 2 is an exploded diagram of another embodiment 60. Embodiment 60 includes an external housing 22-1 and a diffusion membrane 62 which overlies a gas cell 64. Membrane 62 and cell 64 are carried adjacent to a cell-to-PCB gasket 68.

A first combination of optical filter 74a and gasket 74b is positioned adjacent to cell portion 64a. A second, thermal isolating, optical filter 76 is carried adjacent to gasket 74 and reflector 88. Combination 76, 74a provides thermal isolation and filtering of incident radiant energy as explained above relative to elements 34a, 34b of FIG. 1.

A printed circuit board 82a can carry the cell 64. A source of radiant energy 86, such as a lamp or a laser diode or the like along with a reflector 88 complete the cell portion 64b on the printed circuit board 82a. Microphones 40-1 can be carried on a printed circuit board 82b.

Figure 3:
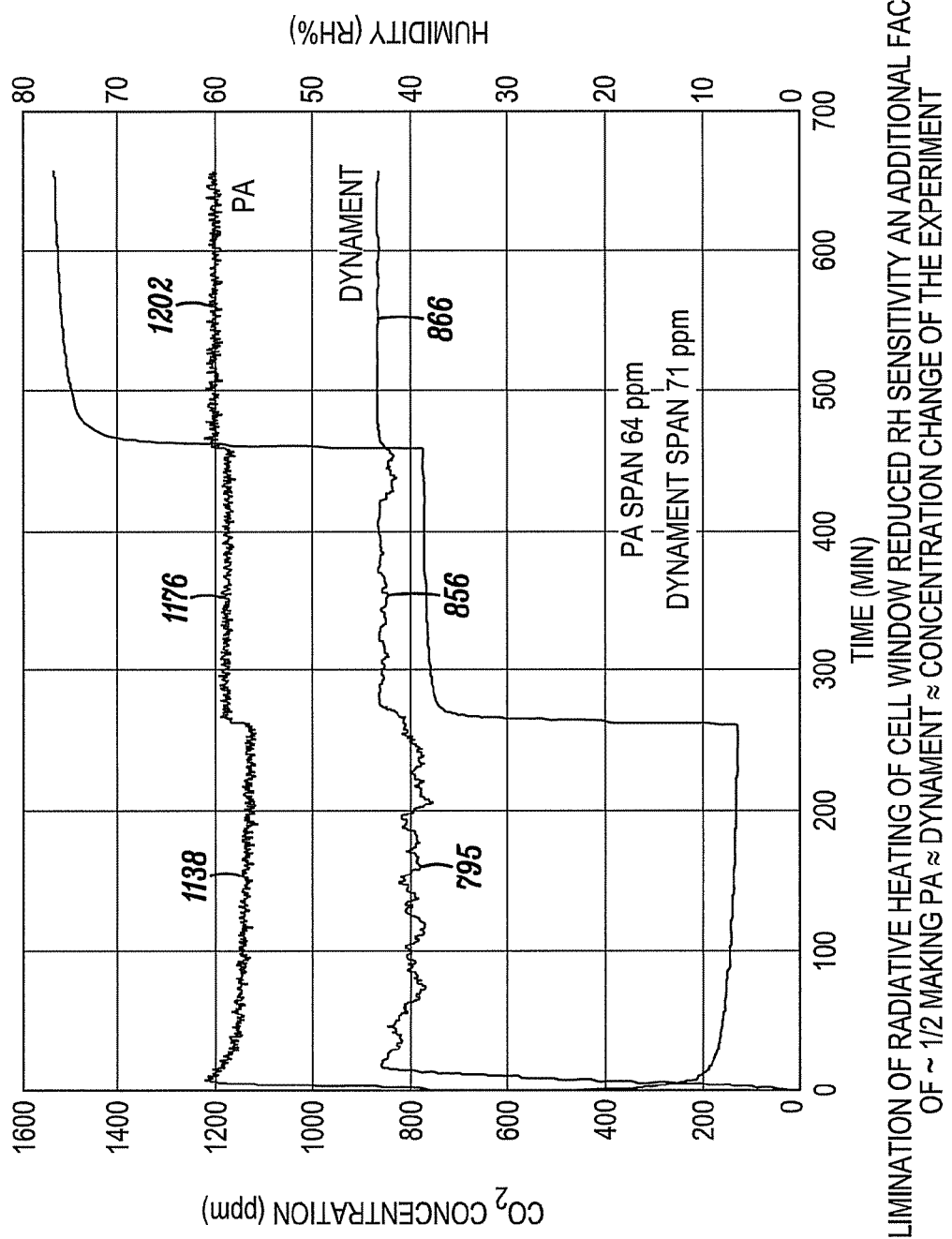
FIG. 3 is a set of graphs which illustrate operational aspects of the detector of FIG. 2.

FIG. 3 is a set of graphs indicating performance of the unit 60 in response to concentration of CO2.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacoustic detector comprising:
    a sensing cell with a gas input port that defines a gas receiving internal region, the cell has a radiant energy receiving port;
    a first optical filter carried adjacent to the cell, the filter covers the receiving port; and
    a thermal isolator,
    wherein the thermal isolator is displaced from the first filter,
    wherein the filter is located between the receiving port and the thermal isolator, and
    wherein a portion of the radiant energy incident on the thermal isolator heats the thermal isolator, thereby thermally isolating the filter therefrom.

2. A detector as in claim 1 which includes a source of radiant energy where the source, the thermal isolator, the first filter and the receiving port are located on a common line that extends from the source to the receiving port.

3. A detector as in claim 1 where the thermal isolator is, at least in part, transmissive of radiant energy.

4. A detector as in claim 2 where the thermal isolator comprises a second optical filter.

5. A detector as in claim 2 where the thermal isolator comprises an optical window transmissive of radiant energy at least over a selected wavelength.

6. A detector as in claim 1 where the filter and the isolator are located on a line that extends there between and through the port.

7. A detector as in claim 6 which includes a reflector positioned at least in part adjacent to the source.

8. A detector as in claim 7 which includes an audio transducer carried adjacent to the cell.

9. A detector as in claim 8 where the cell has an audio output port and the audio transducer is positioned adjacent to the port.

10. A detector as in claim 9 where the transducer comprises a microphone.

11. A detector as in claim 10 which includes a source of radiant energy where the source, the thermal isolator, the first filter and the receiving port are located on a common line that extends from the source to the receiving port.

12. A detector as in claim 10 which includes control circuits coupled at least to the microphone.

13. A detector as in claim 12 where the control circuits process outputs received from the microphone and produce an output signal indicative of a level of sensed gas in the cell.

14. A detector as in claim 13 where the control circuits determine the presence of an alarm condition.

15. A detector as in claim 13 where the control circuits include a programmed processor, and, pre-stored executable instructions.

16. A method comprising:
    providing a sample of ambient atmosphere;
    passing at least a first portion of modulated radiant energy through a thermal isolator;
    heating the thermal isolator with a second portion of the modulated radiant energy, thereby thermally isolating a filter therefrom;
    filtering the first portion of the modulated radiant energy passed through the thermal isolator;
    directing the filtered first portion of the modulated radiant energy toward the sample;
    providing an acoustic output from the sample indicative of gas therein;
    generating an indicator indicative of the presence of gas in the sample.

17. A method as in claim 16 which includes enabling the sample to diffuse into a sampling region through a permeable membrane.

* * * * *